United States Patent [19]

Chang et al.

[11] Patent Number: 5,365,003

[45] Date of Patent: Nov. 15, 1994

[54] SHAPE SELECTIVE CONVERSION OF HYDROCARBONS OVER EXTRUSION-MODIFIED MOLECULAR SIEVE

[75] Inventors: Clarence D. Chang, Princeton; Cynthia T.-W. Chu; Thomas F. Degnan, both of Morrestown; Paul G. Rodewald, Rocky Hill; David S. Shihabi, Pennington, all of N.J.

[73] Assignee: Mobil Oil Corp., Fairfax, Va.

[21] Appl. No.: 22,220

[22] Filed: Feb. 25, 1993

[51] Int. Cl.$^5$ .......................... C07C 5/22; C07C 2/64; C07C 2/02; C10G 73/00
[52] U.S. Cl. .................................. 585/470; 585/475; 585/477; 585/520; 585/446; 585/407; 208/24
[58] Field of Search ............... 585/470, 475, 477, 520, 585/446, 407; 208/24

[56] References Cited

U.S. PATENT DOCUMENTS

| | | |
|---|---|---|
| 3,682,996 | 8/1972 | Kerr . |
| 3,698,157 | 10/1972 | Allen et al. . |
| 4,090,981 | 5/1978 | Rodewald . |
| 4,127,616 | 11/1978 | Rodewald . |
| 4,145,315 | 3/1979 | Rodewald . |
| 4,283,306 | 8/1981 | Herkes . |
| 4,465,886 | 8/1984 | Rodewald . |
| 4,477,583 | 10/1984 | Rodewald . |
| 4,683,214 | 7/1987 | Angevine et al. . |
| 4,843,057 | 6/1989 | D'Amore et al. . |
| 4,851,604 | 7/1989 | Absil et al. . |
| 4,927,979 | 5/1990 | Yamagishi et al. . |
| 4,950,835 | 8/1990 | Wang et al. . |

FOREIGN PATENT DOCUMENTS 296582 12/1988 European Pat. Off. .

OTHER PUBLICATIONS

Hibino, et al. "Journal of Catalysis", 12, 551-558 (1991).

Primary Examiner—Anthony McFarlane
Assistant Examiner—Nhat D. Phan
Attorney, Agent, or Firm—Alexander J. McKillop; Dennis P. Santini; Edward F. Kenehan, Jr.

[57] ABSTRACT

A process for a shape selective hydrocarbon conversion such as toluene disproportionation, involves contacting a reaction stream under conversion conditions with a catalytic molecular sieve which has been preselectivated by agglomerating with an organosilicon compound. The invention also includes a method for agglomeration-preselectivation and the shape selective catalyst which results from the agglomeration preselectivation.

29 Claims, No Drawings

SHAPE SELECTIVE CONVERSION OF HYDROCARBONS OVER EXTRUSION-MODIFIED MOLECULAR SIEVE

CROSS-REFERENCE TO RELATED APPLICATION

This application is related to copending U.S. patent applications Ser. Nos. 850,104 and 850,105 both filed Mar. 12, 1992 which are herein incorporated by reference.

BACKGROUND OF THE INVENTION

1. Field of the Invention

The present invention is directed to a process for shape selective hydrocarbon conversions such as the regioselective production of para-substituted compounds, e.g. para-xylene, over an agglomeration-preselectivated catalyst, a catalyst so selectivated and the method of agglomeration-preselectivating the catalyst. In a toluene disproportionation process, feedstock containing toluene and which may include a high efficiency para-xylene selectivating agent is fed over an agglomeration-preselectivated catalytic molecular sieve.

or the zeolite pore can result in large diffusion changes leading to different product distributions. This type of shape selective catalysis is demonstrated, for example, in toluene selective disproportionation to p-xylene.

The para-xylene may be produced by methylation of toluene over a catalyst under conversion conditions. Examples are the reaction of toluene with methanol as described by Chen et al., J. Amer. Chem. Sec. 1979, 101, 6783, and toluene disproportionation, as described by Pines in "The Chemistry of Catalytic Hydrocarbon Conversions", Academic Press, N.Y., 1981, p. 72. Such methods typically result in the production of a mixture including para-xylene, ortho-xylene, and meta-xylene. Depending upon the para-selectivity of the catalyst and the reaction conditions, different percentages of para-xylene are obtained. The yield, i.e., the amount of feedstock actually converted to xylene, is also affected by the catalyst and the reaction conditions.

Previously known toluene methylation reactions typically provide many by-products such as those indicated in the following formula:

Thermodynamic Equilibria for Toluene Conversion to the Products Indicated

Non-MTPX

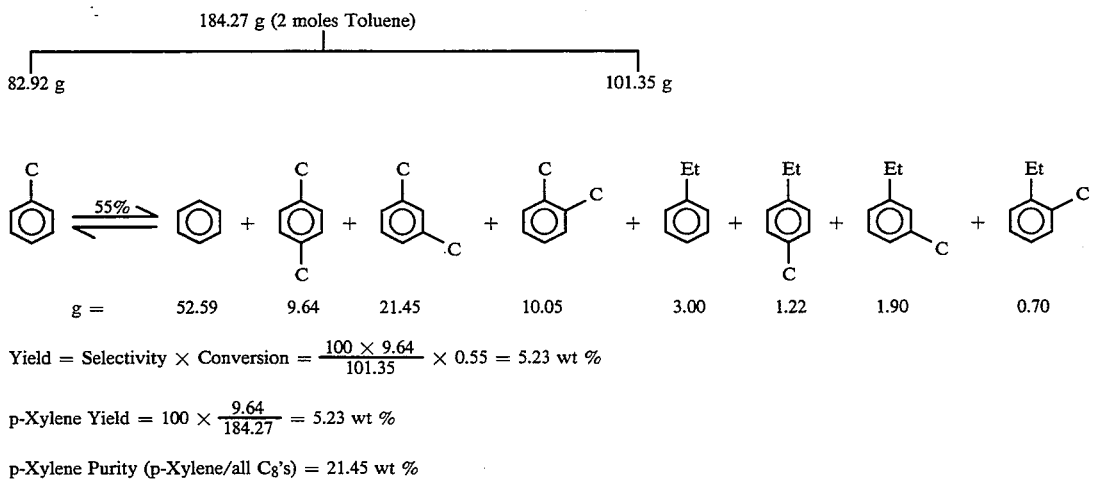

Yield = Selectivity × Conversion = $\frac{100 \times 9.64}{101.35} \times 0.55 = 5.23$ wt % p-Xylene Yield = $100 \times \frac{9.64}{184.27} = 5.23$ wt % p-Xylene Purity (p-Xylene/all C$_8$'s) = 21.45 wt %

2. Description of the Prior Art

The term shape-selective catalysis describes unexpected catalytic selectivities in zeolites. The principles behind shape selective catalysis have been reviewed extensively, e.g. by N. Y. Chen, W. E. Garwood and F. G. Dwyer, "Shape Selective Catalysis in Industrial Applications, 36, Marcel Dekker, Inc. (1989). Within a zeolite pore, hydrocarbon conversion reactions such as paraffin isomerization, olefin skeletal or double bond isomerization, oligomerization and aromatic disproportionation, alkylation or transalkylation reactions are governed by constraints imposed by the channel size. Reactant selectivity occurs when a fraction of the feedstock is too large to enter the zeolite pores to react; while product selectivity occurs when some of the products cannot leave the zeolite channels. Product distributions can also be altered by transition state selectivity in which certain reactions cannot occur because the reaction transition state is too large to form within the zeolite pores or cages. Another type of selectivity results from configurational diffusion where the dimensions of the molecule approach that of the zeolite pore system. A small change in dimensions of the molecule One method for increasing para-selectivity of zeolite catalysts is to modify the catalyst by treatment with "selectivating agents". Various silicon compounds have been used to modify catalysts to improve selectivity in hydrocarbon conversion processes. For example, U.S. Pat. Nos. 4,145,315, 4,127,616, and 4,090,981 describe the use of a silicone compound dissolved in an organic solvent to treat a zeolite. U.S. Pat. Nos. 4,465,886 and 4,477,583 describe the use of an aqueous emulsion of a silicone to treat a zeolite. U.S. Pat. Nos. 4,950,835 and 4,927,979 describe the use of alkoxysilanes carried by gases or organic solvents to treat a zeolite. U.S. Pat. Nos. 4,100,215 and 3,698,157 describe the use of silanes in hydrocarbons, e.g., pyridine, ethers, to treat a zeolite. Such modification methods are known in the art to be carried out after agglomeration of the zeolite. But there has been no suggestion to silicon-modify zeolites during agglomeration.

Some of these catalyst modification procedures, for example, U.S. Pat. Nos. 4,477,583 and 4,127,616 have been successful in obtaining para-selectivity, i.e., para-xylene/all xylenes, of greater than about 90% but with commercially unacceptable toluene conversions of only about 10%, resulting in a yield of not greater than about 9%, i.e., 10%×90%. Such processes also produce significant quantities of ortho-xylene and meta-xylene thereby necessitating expensive separation processes in order to separate the para-xylene from the other isomers.

Typical separation procedures comprise costly fractional crystallization and adsorptive separation of para-xylene from other xylene isomers which are customarily recycled. Xylene isomerization units are then required for additional conversion of the recycled xylene isomers into an equilibrium mixture comprising para-xylene.

Those skilled in the art appreciate that the expense of the separation process is proportional to the degree of separation required. Therefore, significant cost savings are achieved by increasing selectivity to the para-isomer while maintaining commercially acceptable conversion levels.

It is, therefore, highly desirable to provide a regioselective process over a para-selective catalyst for the production of para-xylene from toluene while maintaining commercially acceptable toluene conversion levels. It is also highly desirable to provide an efficient and economical method for preselectivating the catalyst.

SUMMARY OF THE INVENTION

The invention is a process for shape selective hydrocarbon conversions such as the regioselective production of para-xylene. A reaction stream containing toluene is disproportionated over a catalytic molecular sieve which has been preselectivated by agglomeration with an organosilicon compound. Reaction conditions in the toluene disproportionation process over the preselectivated catalyst can provide a single pass para-xylene product, relative to all $C_8$ products, of at least about 90% and at least 15% toluene conversion.

The invention is also a method for modifying a molecular sieve catalyst having a Constraint Index of 1–12 by providing a mixture of molecular sieve crystals, optional binder material and organosilicon compound, subjecting the mixture to agglomeration and calcining the resulting agglomerate. The catalyst may be subsequently contacted with a mixture of a high-efficiency, para-xylene trim selectivating agent and substituted aromatic at reaction conditions for converting toluene to xylene to produce a twice selectivated catalyst. The molecular sieve thus treated has greatly enhanced para-selectivity.

DETAILED DESCRIPTION OF THE INVENTION

The present invention is useful in shape selective hydrocarbon conversion processes such as in converting various aromatics of $C_{6-12}$ e.g., toluene and benzene, to commercially useful para-substituted benzenes, such as para-xylene.

Molecular sieves to be used in the process of the invention include intermediate pore zeolites. Such medium pore zeolites are considered to have a Constraint Index from about 1 to about 12. The method by which Constraint Index is determined is described fully in U.S. Pat. No. 4,016,218, incorporated herein by reference. Molecular sieves which conform to the specified values of Constraint Index for intermediate pore zeolites include ZSM-5, ZSM-11, ZSM-5/ZSM-11 intermediate, ZSM-12, ZSM-21, ZSM-22, ZSM-23, ZSM-35, ZSM-38, ZSM-48, ZSM-50, MCM-22, and Zeolite Beta which are described, for example, in U.S. Pat. Nos. 3,702,886 and Re. No. 29,949, 3,709,979, 3,832,449, 4,046,859, 4,556,447, 4,076,842, 4,016,245, 4,229,424, 4,397,827, 4,954,325, 3,308,069, Re. 28,341 and EP 127,399 to which reference is made for details of these molecular sieves. These zeolites may be produced with differing silica:alumina ratios ranging from 12:1 upwards. Preferred molecular sieves include ZSM-5, ZSM-11, ZSM-12, ZSM-35, ZSM-38 and MCM-22. Particularly preferred is ZSM-5.

In the invention, the catalyst preferably has a silica-alumina ratio less than 100, preferably about 20–80 and an alpha value greater than 100, for example about 150–2000.

The activity of a zeolite is an important consideration in acid-type catalysis such as toluene disproportionation. Silicious zeolites may be considered to contain $SiO_4$-tetrahedra. Substitution for the tetravalent element by a trivalent element such as aluminum produces a negative charge which must be balanced. If this is done by a proton, the material is acidic and active. The activity of zeolite catalysts has been described in terms of its Alpha Value.

The Alpha Value is an approximate indication of the catalytic cracking activity of the catalyst compared to a standard catalyst and it gives the relative rate constant (rate of normal hexane conversion per volume of catalyst per unit time.) It is based on the activity of the amorphous silica-alumina cracking catalyst taken as an Alpha of 1 (Rate Constant=0.016 sec$^{-1}$). The Alpha Test is described in U.S. Pat. No. 3,354,078 and in *The Journal of Catalysis*, Vol. 4, pp. 522–529 (August 1965): Vol. 6, p. 278 (1966); and Vol. 61, p. 395 (1980), each incorporated herein by reference as to that description. It is noted that intrinsic rate constants for many acid-catalyzed reactions are proportional to the Alpha Value for a particular crystalline silicate catalyst (see "The Active Site of Acidic Aluminosilicate Catalysts," *Nature*, Vol. 309, No. 5959, pp. 589–591, Jun. 14, 1984). The experimental conditions of the test used herein include a constant temperature of 538° C. and a variable flow rate as described in detail in the *Journal of Catalysis*, Vol. 61, p. 395.

In the synthesis of zeolites, a reaction mixture is prepared generally containing an oxide of silicon, optionally an aluminum source, a templating agent which is an organic nitrogen containing compound, and an alkaline aqueous medium.

The silicon oxide can be supplied from known sources such as silicates, silica hydrosol, precipitated silica hydrosol, precipitated silica, e.g. Hi-Sil, silica gel, silicic acid. The aluminum oxide may be provided as only an impurity in another reactant, e.g., the silica source.

The sources of organic nitrogen-containing cations, depending, of course, on the particular zeolite product to result from crystallization from the reaction mixture, may be primary, secondary or tertiary amines or quaternary ammonium compounds. Non-limiting examples of quaternary ammonium compounds include salts of tetramethylammonium, tetraethylammonium, tetrapropylammonium, tetrabutylammonium, diethylammonium, triethylammonium, dibenzylammonium, dibenzyldimethylammonium, dibenzyldiethylammonium, benzyltrimethylammonium and chlorine. Non-limiting examples of amines useful herein include the compounds of trimethylamine, triethylamine, tripropylamine, ethylenediamine, propanediamine, butanediamine, pentanediamine, hexanediamine, methylamine, ethylamine, propylamine, butylamine, diamethylamine, diethylamine, dipropylamine, benzylamine, aniline, pyridine, piperidine and pyrrolidine.

The sources of alkali or alkaline earth metal oxide may be, for example, sodium, lithium, calcium, magnesium, cesium or potassium hydroxides, halides (e.g. chlorides, and bromides), sulfates, nitrates, acetates, silicates, aluminates, phosphates and salts of carboxylic acids.

After crystallization of the zeolite, the organic cations are generally removed by calcination or other methods known in the art, and alkali or alkaline earth metals are generally removed, often by intermediate formation of ammonium ion exchange and calcination of the ammonium form to yield the hydrogen form.

After crystallization, zeolite crystals to be used in commercial processes are generally formed into agglomerates for improved strength and resistance to attrition. Various methods are used to agglomerate zeolite crystals. These methods include, for example, extrusion into pellets or beads, spray-drying into fluidizable microspheres, or by hot pressing the zeolite crystals into agglomerates.

The powder form of the crystals can be shaped into a wide variety of particle sizes. Generally speaking, the particles have been shaped into granules, or beads, or a molded product, such as an extrudate having particles size sufficient to pass through a 2 mesh (Tyler) screen and be retained on a 300 mesh (Tyler) screen. In cases where the catalyst is molded, such as by extrusion, the crystals can be extruded before drying or partially dried and then extruded.

In the present invention a silicon-modified zeolite molecular sieve catalyst is prepared by mixing zeolite crystals with an organosilicon compound and optionally a binder material, and agglomerating the mixture, followed by calcination of the agglomerate. Zeolite crystals may be introduced into the mixture in as-synthesized form, and the organic template and alkali or alkaline earth metal ions remaining in the zeolite structure from the crystallization reaction mixture may be removed by methods known in the art after the crystals are agglomerated.

The organosilicon compound is added to the mixture in an aqueous form, for example, as an emulsion which may be surfactant stabilized, as a solution, or as an aerosol. Useful surfactants include, for example, ethers of polyoxyethylene-octylphenols.

The organosilicon compounds include silanes such as alkylsilanes, arylsilanes, alkyarylsilanes, alkoxysilanes, aryloxysilanes, oxyethylenesilanes, alkyaryloxysilanes, siloxanes and polysiloxanes with alkyl and/or aryl and/or glycol groups. Alkyl is intended to include 1 to 12 carbons. Aryl is intended to include 6 to 10 carbons. The organosilicon compounds also include the silicone compounds described below which may also be used in trim selectivation. Preferred are siloxanes such as phenylmethylpolysiloxane.

For the shape selective hydrocarbon conversion process of this invention, the suitable molecular sieve may be agglomerated or extruded in combination with a support or binder material such as, for example, a porous inorganic oxide support or a clay binder. While the preferred binder is silica, other non-limiting examples of such binder materials include alumina, zirconia, magnesia, thoria, titania, boria and combinations thereof, generally in the form of dried inorganic oxide gels or gelatinous precipitates. Suitable clay materials include, by way of example, bentonite and kieselguhr. The relative proportion of suitable crystalline molecular sieve to the total composition of catalyst and binder or support may be about 30 to about 90 percent by weight and is preferably about 50–80 percent by weight of the composition. The composition may be in the form of an extrudate, beads, pellets (tablets) or fluidizable microspheres.

Shape Selective Conversions

Molecular sieves which are selectivation agglomerated in accordance with the invention are generally useful as catalysts in shape selective hydrocarbon conversion processes including cracking reactions involving dewaxing of hydrocarbon feedstocks; isomerization of alkylaromatics; oligomerization of olefins to form gasoline, distillate, lube oils or chemicals; transalkylation of aromatics; alkylation of aromatics; conversion of oxygenates to hydrocarbons, rearrangement of oxygenates, and conversion of light paraffins and olefins to aromatics.

Dewaxing

The subject catalysts have good cracking and hydrocracking activity and may be used to convert paraffins from high to low molecular weight substances in dewaxing processes. The catalysts of the invention may be used in processes such as those described, for example, in U.S. Pat. Nos. 3,700,585, Re. 28,398, 3,968,024 and 4,181,598 which are incorporated herein by reference. The term dewaxing means the removal of those hydrocarbons which will readily solidify (waxes) from petroleum stocks. Hydrocarbon feeds which can be treated include lubricating oil stocks as well as those which have a freeze point or pour point problem, i.e., petroleum stocks boiling above 350° F. The dewaxing can be carried out at either cracking or hydrocracking conditions.

In U.S. Pat. No. 3,700,585 and Re. 28,398 to Chen et al., typical cracking conditions include a liquid hourly space velocity (LHSV) between about 0.5 and 200, a temperature between about 288° C. (550° F.) and 590° C. (1100° F.), a pressure between about subatmospheric and several hundred atmospheres over ZSM-5 type catalysts. Typical hydrocracking conditions include a liquid hourly space velocity between about 0.1 and 10, a temperature between about 340° C. (650° F.) and 538° (1000° F.), a pressure between about 100 and 3000 psig, and a hydrogen to hydrocarbon mole ratio between about one and 20. U.S. Pat. No. 3,968,024 describes similar conversions using ZSM-5 of small crystal size. U.S. Pat. No. 4,181,598 describes shape selective cracking to produce lubes.

Isomerization of alkylaromatics

The modified catalysts of the invention are also advantageously used in the isomerization of alkylaromatics in conversion reactions of the type described, for example, in U.S. Pat. Nos. 3,856,872, 3,856,873, Re. 30,157, 4,101,595, 4,101,597, 4,312,790, Re. 31,919 and 4,224,141 which are herein incorporated by reference.

In U.S. Pat. No. 3,856,872 to Morrison, there is described a process for converting $C_8$ aromatics xylene and ethylbenzene to para-xylene (octafining) at a temperature of 550° F. (288° C.) to 900° F. (482° C.), a pressure of 150 to 300 psig, and a liquid hour space velocity (LHSV) of 1 to 200 over an acid form catalyst containing metal such as platinum or nickel and hydrogen.

In U.S. Pat. No. 3,856,873 to Burress, mixtures of $C_8$ aromatic hydrocarbons are isomerized to para-xylene by contact in vapor phase with zeolite at a temperature of 500° F. (260° C.) to 1000° F. (538° C.), a pressure of 0 (atmospheric) to 1,000 psig, and a WHSV of 0.5 to 250 with no added hydrogen. The catalyst is an acid ZSM-5, ZSM-12 or ZSM-21.

U.S. Pat. No. 4,101,595 to Chen et al. describes the production of para-xylene from aromatics of 8 to 10 carbons over a dual function catalyst with a shape selective acid catalyzed step at a temperature of 650° F. (343° C.) to 1000° F. (538° C.), a pressure of 50 to 500 psig, a LHSV of 0.1 to 100 and a molar ratio of hydrogen/hydrocarbon of 0.1 to 15. The acid form catalyst has a Constraint Index of 1 to 12, a silica/alumina ratio of at least 12, a crystal density of not less than 1.6 g/cc, may be pre-coked, and includes Group VIII noble metal.

In U.S. Pat. No. 4,101,597 to Breckenridge, a $C_8$ feed is first isomerized at 550° F. (288° C.) to 700° F. (371° C.) over a zeolite having a Constraint Index of 1 to 12, a silica/alumina ratio of at least 12 and containing a metal having a hydrogenation/dehydrogenation function. A $C^{9+}$ fraction produced during isomerization of $C_8$ is separated from the other isomerization products, blended with hydrogen and toluene and contacted with a porous, acidic catalyst such as ZSM-5 at 750° (399° C.) to 900° V (482° C.). The catalyst has a Constraint Index of 1 to 12, a silica/alumina ratio of at least 12, and a metal providing hydrogenation/dehydrogenation function.

In U.S. Pat. No. 4,224,141 to Morrison, $C_8$ aromatics are isomerized to benzene, toluene and xylenes over a ZSM-5 which is reduced in activity by dilution with inert matrix, steaming or thermal treatment, very high silica/alumina ratio, base exchange with alkali metal, coking or the like. The conversion is at a temperature of 800° F. (427° C.) to 1000° F. (538° C.) in a low pressure isomerization unit at a pressure only sufficient to overcome pressure drop through downstream processing equipment, e.g. below 100 psig, and a WHSV of 1 to 200.

In U.S. Pat. No. 4,312,790 and Re. 31,919 to Butter et al., a zeolite is incorporated with noble metal subsequent to zeolite crystallization but prior to catalyst extrusion. The catalyst is used for xylene isomerization at a temperature of 500° F. (260° C.) to 1000° F. (540° C.), a pressure between 50 and 1000 psig, a WHSV of 1 to 50 and a hydrogen/hydrocarbon mole ratio of 1 to 20.

Conversion of Oxygenates to Hydrocarbons

U.S. Pat. No. 4,476,330 to Kerr et al. which is herein incorporated by reference describes the conversion of aliphatic oxygenates to a higher molecular weight compound by contacting with a zeolite having a silica/alumina ratio substantially greater than 10 at a temperature of 70° F. (21° C.) to 1400° F. (760° C.). The feeds include lower aliphatic organic oxygenates up to $C_6$, acetals, ketals, acid halides, alcohols, carboxylic acids, aldehydes, acid anhydrides, epoxides, ethers, esters, hemiacetals, gem diols, hydroxy acids, ketones, ketenes, lactones, peracids, peroxides, sugars, and especially alcohols, ethers, and esters.

Oligomerization of olefins

The modified catalysts of the invention are advantageously used in the oligomerization of olefins to form gasoline, distillate, lube oils or chemicals in conversion reactions of the type described, for example, in U.S. Pat. Nos. 4,517,399, 4,520,221, 4,547,609 and 4,547,613 which are herein incorporated by reference.

U.S. Pat. No. 4, 517,399 to Chester et al. describes the conversion of olefins of 3 to 18 carbons, e.g. propylene, to high viscosity, low pour point lubricating oils by contact with ZSM-5 type zeolites having large crystals of at least two microns. The conversion conditions include a temperature of 350° F. (177° C.) to 650° F. (343° C.) a pressure of 100 to 5000 psig, and a WHSV of 0.1 to 10.

U.S. Pat. No. 4,520,221 to Chen describes the polymerization of olefins to 2 to 8 carbons, e.g. propylene, butylene, to high viscosity lubes, e.g. linear hydrocarbons, over highly siliceous, acidic ZSM-5 type catalysts with surface acidity inactivated by treatment with base, e.g. bulky amines with a cross-section larger than about 5 Angstroms. The conversion involves a one or two stage process with the polymerization of lower olefins to linear materials, e.g. at about 200° C. over a surface poisoned zeolite, and oligomerization of the product over a modified or unmodified catalyst at a temperature of 50°-75° C. lower than the first stage, e.g. 150° C. Therefore, the temperatures range from 25° C. to 400° C., with a pressure of atmospheric to 1500 psi and a WHSV of 0.04 to 1.0.

U.S. Pat. No. 4,547,609 to Dessau describes a two stage process whereby in the first stage, light olefins of 2 to 6 carbons are oligomerized to gasoline and distillate liquids including aliphatics of 10 to 20 carbons over a zeolite having a crystal size greater than 0.5 micron at conditions including a temperature of 500° F. (260° C.) or higher, e.g. a range of 500° F. (260° C.) to 800° F. (437° C.), a pressure of atmospheric to 2000 psig and a WHSV of 0.1 to 20. In the second stage, the distillage fraction is converted to high viscosity lubes by contact with a zeolite of smaller crystal size under milder conditions of a temperature about 200° F. (100° C.) to 500° F. (260° C.), a pressure of atmospheric to 650 psig, and a WHSV less than one.

U.S. Pat. No. 4,547,613 to Garwood et al. describes converting olefins of 2 to 16 carbons to high viscosity lube oil. A ZSM-5 type catalyst is pre-conditioned by contact with light olefins of 2 to 16 carbons, e.g. propylene at 400° F. (204° C.) to 1000° F. (538° C.), at a pressure of 0 to 100 psig for 1 to 70 hours. Conversion conditions include a temperature of 350° F. (177° C.) to 650° F. (343° C.), a pressure of 400 to 5000 psig and a WHSV of 0.1 to 10. The lube fractions may be subjected to a hydrogenation step to stabilize.

Conversion of aromatics to dialkyl-substituted benzene

The modified zeolite catalysts of the invention are advantageously used in the conversion of aromatics compounds to provide dialkyl-substituted benzene products which are highly enriched in the para-dialkyl substituted benzene isomer. Conversion reactions of this type include aromatics alkylation, transalkylation and disproportionation. Aromatics alkylations in which the catalysts of the invention can be used are described, for example, in U.S. Pat. Nos. 3,755,483, 4,086,287, 4,117,024 and 4,117,026 which are herein incorporated by reference.

As described in U.S. Pat. No. 3,755,483 to Burress, aromatic hydrocarbons such as benzenes, naphthalenes, anthracenes and substituted derivatives thereof, e.g. toluene and xylene, may be alkylkated with alkylating agents such as olefins ethylene, propylene, dodecene, and formaldehyde, alkyl halides, and alkyl alcohols with 1 to 24 carbons under vapor phase conditions including a reactor inlet temperature up to about 900° F. (482° C.), with a reactor bed temperature up to about 1050° F. (566° C.), at a pressure of about atmospheric to about 3000 psig, a ratio of aromatic/alkylating agent of about 1:1 to about 20:1 and a WHSV of 20 to 3000 over ZSM-12.

As described in U.S. Pat. No. 4,086,287 to Kaeding et al., monoalkylbenzenes having alkyls of 1-2 carbons, such as toluene and ethylbenzene, may be ethylated to produce a para-ethyl derivative, e.g. para-ethyltoluene at a temperature of from about 250° C. to about 600° C., a pressure of 0.1 atmospheres to 100 atmospheres, a weight hourly space velocity (WHSV) of 0.1 to 100, and a ratio of feed/ethylating agent of 1 to 10 over a catalyst having an acid activity, i.e., alpha, of 2 to 5000, modified by precoking or combining with oxides of phosphorus, boron or antimony to attain a catalyst with a xylene sorption capacity greater than 1 g/100 g of zeolite and an ortho-xylene sorption time for 30% of said capacity of greater than 10 minutes, where sorption capacity and sorption time are measured at 120° C. and a xylene pressure of 4.5±0.8 mm of mercury.

U.S. Pat. No. 4,117,024 to Kaeding describes a process for the ethylation of toluene or ethylbenzene to produce p-ethyltoluene at a temperature of 350° C. to 550° C., a critical pressure of greater than one atmosphere and less than 400 psig, with hydrogen/ethylene ratio of 0.5 to 10 to reduce aging of the catalyst. The zeolite described in U.S. Pat. No. 4,117,024 has a crystal size greater then one micron, and is modified as the catalyst in U.S. Pat. No. 4,086,287 to attain the sorption capacity described in U.S. Pat. No. 4,086,287.

U.S. Pat. No. 4,117,026 to Haag and Olsen describes the production of para-dialkyl benzenes having alkyls of 1 to 4 carbons under conditions which vary according to the feed. When the feed includes monoalkyl substituted benzenes having an alkyl of 1 to 4 carbons, olefins of 2 to 15, or paraffins of 3 to 60 carbons or mixtures thereof, conversion conditions include a temperature of 250° C. to 750°, a pressure of 0.1 to 100 atmospheres and a WHSV of 0.1 to 2000. For the disproportionation of toluene, the conditions include a temperature of 400° C. to 700° C., a pressure of 1 to 100 atmospheres, and an a WHSV of 1–50. When the feed includes olefins of 2 to 15 carbons including cyclic olefins, the conversion conditions include a temperature of 300° C. to 700° C., a pressure of 1 to 100 atmospheres and a WHSV of 1 to 1000. When the feed includes paraffins of 3 to 60 carbons, conditions include a temperature of 300° C. to 700° C., a pressure of 1 to 100 atmospheres and a WHSV of 0.1 to 100. However for lower paraffins of 3 to 5 carbons, the temperature should be above 400° C. When the feed includes mixed aromatics such as ethylbenzene and toluene, and also optionally olefins of 2 to 20 carbons or paraffins of 5 to 25 carbons, conversion conditions include a temperature of 250° C. to 500° C. and a pressure greater than 200 psig. In the absence of added aromatics, the olefins and higher paraffins are more reactive and require lower severity of operations, e.g. a temperature of 250° C. to 600° C. preferable 300°–550° C. The catalyst described in U.S. Pat. No. 4,117,026 is modified as in U.S. Pat. No. 4,086,287.

Conversion of light paraffins and olefins to aromatics

The modified catalysts of the invention may also be used in the conversion of light paraffins and olefins to aromatics in processes of the type described, for example, in U.S. Pat. Nos. 3,760,024 and 3,756,942 which are herein incorporated by reference.

U.S. Pat. No. 3,760,024 to Cattanach describes a process for the conversion of paraffins of 2 to 4 carbons and/or olefins to aromatics of 6 to 10 carbons over a ZSM-5 type catalyst with or without hydrogenation/dehydrogenation component. Conversion conditions include a temperature of 100° C. to 650° C., a pressure of 0 to 1,000 psig, a WHSV of 0.1 to 500 and a hydrogen/hydrocarbon ratio of 0 to 20.

U.S. Pat. No. 3,756,942 to Cattanach describes the conversion of paraffins, olefins and naphthenes to aromatics over ZSM-5 type catalysts. If the feed contains at least 35 wt. % olefins, conversion is at 650° F. (363° C.) to 1400° F. (760° C.). If the feed contains less than 35 wt. % olefins, the temperature is 900° F. (482° C.) to 1400° F. (760° C.) with the absence of substantial added hydrogen. For both types of feed, the pressure is atmospheric to 35 atmospheres and the WHSV 1 to 15.

Pyridine synthesis

The modified catalysts of the invention are also advantageously used in the synthesis of pyridine. Pyridine bases may be produced through the reactions of aldehydes and ketones with ammonia. The reaction of acetaldehyde with ammonia in the presence of heterogenous catalysts at about 350° C. to about 550° C. yields 2-and 4-methylpyridine. Acetaldehyde, formaldehyde and ammonia react to yield pyridine and 3-methylpyridine. Pyridine synthesis is described, for example, in U.S. Pat. No. 4,220,783 to Chang et al. and U.S. Pat. No. 4,675,410 to Feitler which are herein incorporated by reference.

Caprolactam synthesis

Caprolactam is used in the commercial production of nylon. The cyclohexanone precursor of caprolactam is produced from benzene by phenol dehydrogenation or cyclohexane oxidation over a catalyst containing palladium in liquid or vapor phase. Caprolactam may be produced by Beckmann rearrangement of cyclohexane oxime over acid catalysts including zeolites. The synthesis of caprolactam is described, for example, in U.S. Pat. No. 4,359,421 which is herein incorporated by reference.

Therefore, the modified catalysts of the present invention are suitable for use in a variety of shape selective hydrocarbon conversion processes including as non-limiting examples, cracking hydrocarbons with reaction conditions including a temperature of from about 300° C. to about 700° C., a pressure of from about 0.1 atmosphere (bar) to about 30 atmospheres and a weight hourly space velocity of from about 0 1 $hr^{-1}$ to about 20 $hr^{-1}$; dehydrogenating hydrocarbon compounds with reaction conditions including a temperature of from about 300° C. to about 700° C., a pressure of from about 0.1 atmosphere to about 10 atmospheres and a weight hourly space velocity of from about 0.1 to about 20; converting paraffins to aromatics with reaction conditions including a temperature of from about 300° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20: converting olefins to aromatics, e.g. benzene, toluene and xylene, with reaction conditions including a temperature of from about 0.1 atmosphere to about 60 atmospheres, a weight hourly space velocity of from about 0.5 to about 400 and a hydrogen/hydrocarbon mole ratio of from about 0 to about 20: converting alcohols, e.g. methanol, or ethers, e.g. dimethylether, or mixtures thereof to hydrocarbons including olefins and/or aromatics with reaction conditions including a temperature of from about 275° C. to about 600° C., a pressure of from about 0.5 atmosphere to about 50 atmospheres and a liquid hourly space velocity of from about 0.5 to 100; isomerizing xylene feedstock components with reaction conditions including a temperature of from about 230° C. to about 510° C., a pressure of from about 3 atmospheres to about 35 atmospheres, a weight hourly space velocity of from about 0.1 to about 200 and a hydrogen/hydrocarbon mole ratio of from about 0 to about 100; disproportionating toluene with reaction conditions including a temperature of from about 200° C. to about 760° C., a pressure from about atmospheric to about 60 atmospheres and a weight hourly space velocity of from about 0.08 to about 20; alkylating aromatic hydrocarbons, e.g. benzene and alkylbenzenes in the presence of an alkylating agent, e.g. olefins, formaldehyde, alkyl halides and alcohols, with reaction conditions including a temperature of from about 250° C. to about 500° C., a pressure of from about atmospheric to about 200 atmospheres, a weight hourly space velocity of from about 2 to about 2000 and an aromatic hydrocarbon/alkylating agent mole ratio of from about 1/1 to about 20/1; and transalkylkating aromatic hydrocarbons in the presence of polyalkylaromatic hydrocarbons with reaction conditions including a temperature of from about 340° C. to about 500° C., a pressure of from about atmospheric to about 200 atmospheres, a weight hourly space velocity of from about 10 to about 1000 and an aromatic hydrocarbon/polyalkylaromatic hydrocarbon mole ratio of from about 1/1 to about 16/1.

In general, therefore, catalytic conversion conditions over a catalyst comprising the modified zeolite include a temperature of from about 100° C. to about 760° C., a pressure of from about 0.1 atmosphere (bar) to about 200 atmospheres (bar), a weight hourly space velocity of from about 0.08 hr$^{-1}$ to about 2000 hr$^{-1}$ and a hydrogen/organic, e.g. hydrocarbon compound of from 0 to about 100.

Toluene Disproportionation

Toluene Disproportionation will be used as a representative shape selective conversion. Reaction conditions in the toluene disproportionation contemplated herein include temperatures ranging from about 100° C. to about 600° C., preferably from about 300° C. to about 500° C.; pressures ranging from about 0 to about 2000 psig, preferably from about 15 to about 800 psig; a mole ratio of hydrogen to hydrocarbons from about 0 (i.e. no hydrogen is present) to about 10, preferably from about 1 to about 4; at a weight hourly space velocity (WHSV) from about 0.1 to about 100 hr$^{-1}$, preferably from about 0.1 to about 10 hr$^{-1}$.

Normally a single pass conversion of a toluene stream results in a product stream which includes dimethylbenzenes having alkyl groups at all locations, i.e., ortho-, meta-, and para-xylenes. Furthermore, the xylenes are known to proceed in a reaction which produces unwanted ethylbenzenes (EB) by the following reaction:

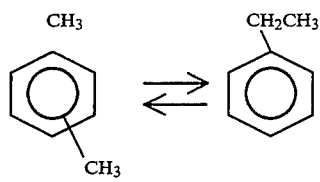

Previously, the purity of p-xylene with respect to all of the $C_8$ products in a single pass has been limited to less than 90% when isomerization is permitted. This efficiency is reduced somewhat by the production of ethylbenzene.

The present invention, however, provides high efficiency conversion which reduces production of ortho- and meta-isomers to the benefit of the desired para-isomer. The resulting product stream contains greater than a 90% purity of para-xylene. For example, the ortho-xylene isomer can be reduced to not more than about 0.5% of the total xylenes content while the meta-xylene isomer can be reduced to less than about 5% of the total xylene content. Moreover, when the reaction system is properly treated, such as by deposition of platinum on the molecular sieve, the presence of ethylbenzene can be reduced to less than about 0.3% of the $C_8$ product.

As explained in greater detail herein, the present invention provides a method for obtaining para-xylene at conversion rates of at least about 15%, preferably at least about 20–25%, and with para-xylene purity of greater than 90%, preferably at least 95%, and most preferably about 99%.

Therefore higher para-xylene purity can be attained at commercially acceptable conversion rates than with previously disclosed processes. The present invention thus allows for a significant reduction in process costs previously associated with the separation of unwanted by-products. Toluene disproportionation processes of the prior art typically require expensive secondary and tertiary treatment procedures in order to obtain these efficiencies.

The present invention includes the regioselective conversion of toluene to para-xylene by methylating toluene in a reaction stream containing a toluene feed with a trim selectivated catalytic molecular sieve which has been pre-selectivated as described above with conversion reaction conditions to provide a single pass, para-xylene purity of at least about 90% based on the $C_8$ products. The trim selectivation methods are described below. As used herein, the term "para-xylene purity" means the percentage of para-xylene in all of the $C_8$ products which include ethylbenzene, para-xylene, ortho-xylene, and meta-xylene. Those skilled in the art will appreciate that the proximity of the boiling points of these $C_8$ products necessitates more expensive separation processes whereas para-xylene may be more readily separated from other components in the product stream such as benzene, toluene, and para-ethyltoluene.

As used herein, the term "xylene-conversion product" indicates the total amount of xylenes resulting from the disproportionation reaction. The word "para-xylene" in this term is not intended to limit the scope of the present invention to the production of xylenes since other para-substituted aromatics may be produced.

In a preferred embodiment, the invention also includes a method for the regioselective production of para-xylene by passing a reaction stream which contains an aromatic feedstock, e.g., toluene, in a single pass, over a trim-selectivated catalytic molecular sieve, which is pre-selectivated, the single pass in the presence of hydrogen at reaction conditions suitable to provide para-xylene purity of greater than about 90%. The product stream may also include small amounts of ortho- and meta-xylene and trace amounts of impurities such as ethylbenzene.

The toluene may be fed simultaneously with a high-efficiency selectivating agent and hydrogen at reaction conditions until the desired p-xylene selectivity, e.g., 90% or 95%, is attained, whereupon the feed of selectivating agent is discontinued. This co-feeding of selectivating agent with toluene will be termed "trim selectivation". Reaction conditions for this trim-selectivation step generally include a temperature of about 350°-540° C. and a pressure of about atmospheric—5000 psig. The feed is provided to the system at a rate of about 0.1-20 WHSV. The hydrogen is fed at a hydrogen to hydrocarbon molar ratio of about 0.1-20.

The high efficiency para-xylene selectivating agent for trim selectivation preferably comprises a silicon containing compound discussed in greater detail below. For example, organic silicons such as phenylmethyl silicone, dimethyl silicone, and mixtures thereof are suitable. According to one embodiment of the present invention, a silicone containing phenylmethylsilicone and dimethylsilicone groups in a ratio of about 1:1 is co-fed to the system, while the other components, e.g., toluene and hydrogen, are fed in the amounts set forth above. The high-efficiency para-xylene selectivating agent is fed in an amount of about 0.1%-50% of the toluene according to this preferred embodiment. Depending upon the percentage of selectivating agent used, the trim selectivation will preferably last for about 50-300 hours, most preferably less than 170 hrs.

The catalyst is modified by ex situ pre-selectivation during agglomeration by mixing zeolite with an organosilicon compound, followed by agglomeration of the mixture, then calcination of the agglomerate. The mixture may also include binder material. After pre-selectivation, the catalytic molecular sieves for the present invention are preferably converted to the hydrogen and optionally, a Group VIII metal form. The crystal size of zeolites used herein is preferably greater than 0.1 micron. Subsequently the preselectivated agglomerate may be trim selectivated with a high efficiency para-xylene selectivating agent.

As used herein, the term "high efficiency, p-xylene selectivating agent" as used for trim selectivation is used to indicate substances which will increase the para-selectivity of a catalytic molecular sieve to the stated levels while maintaining commercially acceptable toluene to xylene conversion levels. Such substances include, for example, organic silicon compounds such as phenylmethyl silicone, dimethylsilicone, and blends thereof which have been found to be suitable.

The trim selectivation of the catalyst is preferably performed with a silicone containing compound. An example of silicone compounds which can be used in the present invention can be characterized by the general formula:

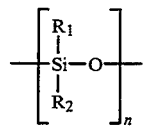

where $R_1$ is hydrogen, fluorine, hydroxy, alkyl, aryl, alkylaryl or fluoro-alkyl. The hydrocarbon substituents generally contain from 1 to 10 carbon atoms and preferably are methyl or ethyl groups. $R_2$ is selected from the same group as $R_1$, and n is an integer of at least 2 and generally in the range of 3 to 1000. The molecular weight of the silicone compound employed is generally between about 80 and about 20,000 and preferably within the approximate range of 150 to 10,000. Representative silicone compounds include dimethylsilicone, diethylsilicone, phenylmethylsilicone, methylhydrogensilicone, ethylhydrogensilicone, phenylhydrogensilicone, methylethylsilicone, phenylethylsilicone, diphenylsilicone, methyltrifluoropropylsilicone, ethyltrifluoropropysilicone, polydimethylsilicone, tetrachlorophenylmethyl silicone, tetrachlorophenylethyl silicone, tetrachlorophenylhydrogen silicone, tetrachlorophenylphenyl silicone, methylvinylsilicone and ethylvinylsilicone. The silicone compound need not be linear but may be cyclic as for example hexamethylcyclotrisiloxane, octamethylcyclotetrasiloxane, hexaphenylcyclotrisiloxane and octaphenylcyclotetrasiloxane. Mixtures of these compounds may also be used as well as silicones with other functional groups. Other silicon-containing compounds, such as silanes and siloxanes, may also be utilized.

Preferably, the kinetic diameters of the high efficiency, p-xylene trim selectivating agent and the selectivating silicon compounds added during zeolite agglomeration are larger than the zeolite pore diameter, in order to avoid reducing the internal activity of the catalyst.

Before trim-selectivation, the catalyst is pre-selectivated during, for example, extrusion, and a silicon compound is deposited on the external surface of the molecular sieve catalyst.

Following deposition of the silicon-containing compound in pre-selectivation, the catalyst is calcined. For example, the catalyst may be calcined in an oxygen-containing atmosphere, preferably air, at a rate of 0.2° to 5° C./minute to a temperature greater 300° C. but below a temperature at which the crystallinity of the zeolite is adversely affected. Generally, such temperature will be below 600° C. Preferably the temperature of calcination is within the approximate range of 350° to 550° C. The product is maintained at the calcination temperature usually for 1 to 24 hours.

While not wishing to be bound by theory, it is believed that the advantages of the present invention are obtained by rendering acid sites on the external surfaces of the catalyst substantially inaccessible to reactants while increasing catalyst tortuosity. Acid sites existing on the external surface of the catalyst are believed to isomerize the para-xylene exiting the catalyst pores back to an equilibrium level with the other two isomers thereby reducing the amount of para-xylene in the xylenes to only about 24%. By reducing the availability of these acid sites to the para-xylene exiting the pores of the catalyst, the relatively high level of para-xylene can be maintained. It is believed that the high-efficiency, p-xylene selectivity agents of the present invention block or otherwise render these external acid sites unavailable to the para-xylene by chemically modifying said sites.

In line with this theory, it is also believed that the presence of hydrogen in the reaction zone during the trim selectivation is important in order to maintain the desired high yields of para-xylene when a silicone compound is used as the high-efficiency para-xylene selectivating agent. The importance of the hydrogen may be reduced in alternative embodiments by using a high efficiency para-xylene selectivating agent comprising silane or some other compound which effectively renders the isomerizing acid sites on the external surface of the catalyst inaccessible.

The invention may utilize a high efficiency para-xylene selectivating agent which includes a silicon compound wherein the silicon compound is introduced by co-feeding, for example, at least one silicon compound with the toluene feedstock over a conversion catalyst at reaction conditions until the desired degree of selectivation is achieved, at which time the feed of selectivating agent may be discontinued.

The toluene feedstock preferably includes about 50% to 100% toluene, more preferably at least about 80% toluene in the toluene feedstock. Other compounds such as benzene, xylenes, and trimethylbenzene may also be present in the toluene feedstock without adversely affecting the present invention.

The toluene feedstock may also be dried, if desired, in a manner which will minimize moisture entering the reaction zone. Methods known in the art suitable for drying the toluene charge for the present process are numerous. These methods include percolation through any suitable desiccant, for example, silica gel, activated alumina, molecular sieves or other suitable substances, or the use of liquid charge dryers.

Operating conditions employed in the improved process of the present invention may be adjusted to affect the para-selectivity and toluene conversion rate. Such conditions include the temperature, pressure, space velocity, molar ratio of the reactants, and the hydrogen to hydrocarbon mole ratio. One preferred embodiment of the present invention includes contacting a catalytic molecular sieve with a toluene feedstock which includes a silicone compound under conditions for effecting vapor-phase disproportionation. Conditions effective for accomplishing the high para-selectivity and acceptable toluene disproportionation conversion rates include a reactor inlet temperature of about 350°–540° C., preferably greater than about 400° C., a pressure of about atmospheric—5000 psig, preferably about 100 to 1000 psig, a WHSV of about 0.1–20, preferably about 2–4, and a hydrogen to hydrocarbon mole ratio of about 0.1–20, preferably about 2–4. This process may be conducted in either batch or fluid bed operation with attendant benefits of either operation readily obtainable.

The effluent is separated and distilled to remove the desired product, i.e., para-xylene, plus other by-products.

The catalyst may be further modified in order to reduce the amount of undesirable by-products, particularly ethylbenzene. The state of the art is such that the reactor effluent from standard toluene disproportionation typically contains about 0.5% ethylbenzene by-product. Upon distillation of the reaction products, the level of ethylbenzene in the $C_8$ fraction often increases to about 3–4 percent. This level of ethylbenzene is unacceptable for polymer grade p-xylene since ethylbenzene in the $C_8$ product, if not removed, degrades the quality of fibers ultimately produced from the p-xylene product. Consequently, ethylbenzene content must be kept low. The specification for ethylbenzene in the $C_8$ product has been determined by industry to be less than 0.3%. Ethylbenzene can be substantially removed by isomerization or by superfractionation processes. Removal of the ethylbenzene by conventional isomerization would be impractical with the present invention since the xylene stream, which includes greater than 90% para-xylene, would be concurrently isomerized to equilibrium xylenes reducing the amount of para-xylene in this xylene stream to about 24%. It is known in the art that the alternative procedure of removing the ethylbenzene by superfractionation is extremely expensive.

In order to avoid the need for downstream ethylbenzene removal, the level of ethylbenzene by-product is advantageously reduced by incorporating a hydrogenation-dehydrogenation function in the catalyst, such as by addition of a metal compound such as platinum. While platinum is the preferred metal, other metals such as palladium, nickel, copper, cobalt, molybdenum, rhodium, ruthenium, silver, gold, mercury, osmium, iron, zinc, cadmium, and mixtures thereof may be utilized. The metal may be added by cation exchange, in amounts of about 0.01–2%, typically about 0.5%. The metal must be able to enter the pores of the catalyst in order to survive a subsequent calcination step. For example, a platinum modified catalyst can be prepared by first adding the catalyst to a solution of ammonium nitrate in order to convert the catalyst to the ammonium form. The catalyst is subsequently contacted with an aqueous solution of tetraamine platinum(II) nitrate or tetraamine platinum(II) chloride. The metallic compound advantageously enters the pores of the catalyst. The catalyst can then be filtered, washed with water and calcined at temperatures of about 250° to 500° C.

By the present process, toluene can be converted to aromatic concentrates of high value, e.g., about 99% para-xylene based on all $C_8$ products. In a typical embodiment of the present process, optimum toluene conversion is found to be about 20–25 weight percent with a para-xylene purity of about 90–99%.

The following non-limiting examples illustrate the invention:

EXAMPLE 1

To 15.57 g distilled water in a 150 cc beaker was added 1.01 g 50% sodium hydroxide solution and 2.20 g dimethyl silicon modified with oxyethylene groups to render it water soluble to 38C° . To this solution was added a mixture of 10.85 g as-synthesized ZSM-5 and 5.85 g hydrated amorphous silica with stirring. The resultant dry paste was extruded using a hand extruder to give well-formed 1/16 inch extrudate. Drying at 120° C. for two hours gave 12.91 g product.

EXAMPLE 2

To 15.58 g distilled water in a 150 cc beaker was added 1.03 g 50% sodium hydroxide solution and a mixture of 4.06 g phenylmethylpolysiloxane and 0.79 g iso-Octylphenoxypolyethoxyethanol surfactant to form an emulsion. To this emulsion was added a mixture of 10.85 g as-synthesized ZSM-5 and 5.85 g hydrated amorphous silica (HiSil, PPG Industries, Inc.) with stirring. The resultant dry paste was extruded using a hand extruder to give well-formed 1/16 inch extrudate. Drying at 120° C. for two hours gave 13.49 g product.

What is claimed is:

1. A process for a shape selective hydrocarbon conversion comprises contacting a reaction stream comprising hydrocarbon under conversion conditions, with a catalytic molecular sieve which has been pre-selectivated by agglomerating a mixture comprising crystalline molecular sieve material and organosilicon compound.

2. The process of claim 1 wherein the shape selective hydrocarbon conversion is selected from a group consisting of dewaxing of paraffins, isomerization of alkylaromatics, oligomerization of olefins, transalkylation of aromatics, alkylation of aromatics, conversion of oxygenates to hydrocarbons, rearrangement of oxygenates and conversion of paraffins and olefins to aromatics.

3. The process of claim 1 wherein the conversion conditions comprise a temperature of from about 100° C. to about 760° C., a pressure of about 0.1 atmosphere to about 100 atmospheres, a weight hourly space velocity of from about 0.08 $hr^{-1}$ to about 200 $hr^{-1}$, and a hydrogen/hydrocarbon molar ratio of from about 0 to about 100.

4. The process of claim 1 wherein the shape selective hydrocarbon conversion is toluene disproportionation.

5. The process of claim 1 wherein the molecular sieve has a Constraint Index from about 1 to about 12.

6. The process of claim 1 wherein after being pre-selectivated the molecular sieve is ion exchanged to contain ions selected from a group consisting of hydrogen, hydrogen precursor, metals of Periodic Table Group VIII and combinations thereof.

7. The process of claim 1 wherein the mixture comprising crystalline molecular sieve material and organosilicon compound further comprises a matrix material.

8. The process of claim 7 wherein the matrix material comprises amorphous silica.

9. The process of claim 1 wherein the organosilicon compound is selected from a group consisting of silicones, silanes, alkoxysilanes, siloxanes and polysiloxanes.

10. The process of claim 9 wherein the organosilicon compound is added to the mixture in an aqueous form selected from a group consisting of solutions, aerosols, emulsions and surfactant-stabilized emulsions.

11. The process of claim 10 wherein the surfactant-stabilized aqueous emulsion includes a surfactant which is a polyoxyethylene-octylphenol ether.

12. The process of claim 9 wherein the organosilicon compound is a polysiloxane.

13. The process of claim 12 wherein the polysiloxane is phenylmethylpolysiloxane.

14. A process for disproportionation of toluene into p-xylene comprising:

contacting a reaction stream comprising toluene under toluene disproportionation conditions with a catalytic molecular sieve which has been pre-selectivated by agglomerating a mixture comprising crystalline molecular sieve material and an organosilicon compound.

15. The process of claim 14 wherein said catalytic molecular sieve comprises a Constraint Index of about 1 to 12, and said reaction conditions comprise a temperature of about 350° C. to about 540° C., a pressure of from about atmospheric to about 5000 psig, a WHSV of from about 0.1 to about 20, and a hydrogen to hydrocarbon molar ratio of from about 0.1 to about 20.

16. The process of claim 14 wherein after being pre-selectivated the molecular sieve is ion exchanged to contain ions selected from a group consisting of hydrogen, hydrogen precursor, metals of Periodic Table Group VIII and combinations thereof.

17. The process of claim 14 wherein the mixture comprising crystalline molecular sieve material and organosilicon compound further comprises a matrix material.

18. The process of claim 17 wherein the matrix material comprises amorphous silica.

19. The process of claim 14 wherein the organosilicon compound is selected from a group consisting of silicones, silanes, alkoxysilanes, siloxanes and polysiloxanes.

20. The process of claim 14 wherein the organosilicon compound is added to the mixture in an aqueous form selected from a group consisting of solutions, aerosols, emulsions and surfactant-stabilized emulsions.

21. The process of claim 20 wherein the surfactant-stabilized aqueous emulsion includes a surfactant which is a polyoxyethylene-octylphenol ether.

22. The process of claim 14 wherein the organosilicon compound is a polysiloxane.

23. The process of claim 22 wherein the polysiloxane is phenylmethylpolysiloxane.

24. The process of claim 14 wherein the reaction stream further comprises a second silicon-containing compound which is a high efficiency para-xylene selectivating agent.

25. The process of claim 24 wherein the high efficiency para-xylene selectivating agent comprises a silicone compound.

26. The process of claim 25 wherein the silicone compound comprises a mixture of phenylmethylsilicone and dimethylsilicone.

27. The process of claim 25 wherein the reaction stream comprises at least 80 wt. % of toluene and at least 0.1 wt. % silicone.

28. The process of claim 25 wherein the silicone compound is fed with the reaction stream for at least one hour.

29. The process of claim 24 wherein the contacting provides a single pass para-xylene product purity, relative to all xylene products of at least 90 wt. % with at least about 15 wt. % toluene conversion.

* * * * *